(12) United States Patent
Cao et al.

(10) Patent No.: US 10,256,306 B1
(45) Date of Patent: Apr. 9, 2019

(54) VERTICALLY INTEGRATED MULTISPECTRAL IMAGING SENSOR WITH GRAPHENE AS ELECTRODE AND DIFFUSION BARRIER

(71) Applicant: INTERNATIONAL BUSINESS MACHINES CORPORATION, Armonk, NY (US)

(72) Inventors: Qing Cao, Yorktown Heights, NY (US); Ning Li, Yorktown Heights, NY (US); Jianshi Tang, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/827,785

(22) Filed: Nov. 30, 2017

(51) Int. Cl.
| | | |
|---|---|---|
| *H01L 31/00* | (2006.01) | |
| *H01L 29/16* | (2006.01) | |
| *H04N 5/33* | (2006.01) | |
| *H01L 27/146* | (2006.01) | |
| *G01N 21/25* | (2006.01) | |
| *G01J 3/447* | (2006.01) | |
| *G01N 21/31* | (2006.01) | |
| *G01J 3/28* | (2006.01) | |

(52) U.S. Cl.
CPC .......... *H01L 29/1606* (2013.01); *G01J 3/447* (2013.01); *G01N 21/255* (2013.01); *H01L 27/14601* (2013.01); *H04N 5/332* (2013.01); *G01J 2003/2826* (2013.01); *G01N 21/314* (2013.01)

(58) Field of Classification Search
CPC ............ H01L 29/1606; H01L 27/14601; G01J 3/447; G01J 2003/2826; G01N 21/255; G01N 21/314; H04N 5/332
USPC ......................................................... 257/440
See application file for complete search history.

(56) References Cited

U.S. PATENT DOCUMENTS

| | | | |
|---|---|---|---|
| 9,067,783 B2 * | 6/2015 | Choi ......................... | G01J 1/42 |
| 9,496,315 B2 | 11/2016 | Forrest et al. | |
| 9,899,547 B2 * | 2/2018 | Engel ................... | H01L 31/109 |
| 2011/0049489 A1 | 3/2011 | Forrest et al. | |

FOREIGN PATENT DOCUMENTS

| | | |
|---|---|---|
| CN | 105185800 | 12/2015 |
| CN | 105426384 | 3/2016 |

OTHER PUBLICATIONS

Written Opinion dated Jan. 30, 2019 for International Application No. PCT/IB2018/059296.

* cited by examiner

*Primary Examiner* — Tu-Tu V Ho

(57) ABSTRACT

A vertically integrated multispectral imaging sensor includes a first metal contact layer on a substrate, an $SiO_2$ layer on the first metal contact layer with a first detector element embedded in a hole therein, a first graphene layer that covers the first detector element, a second metal contact layer on the $SiO_2$ layer on one side of the first graphene, an $AlO_3$ layer on the $SiO_2$ layer, in which a second detector element is embedded in a hole over the first graphene layer, a second graphene layer on the second detector element, and a third metal contact layer on the $AlO_3$ layer adjacent to the second graphene layer. The first detector material is sensitive to a different wavelength band of the electromagnetic spectrum than the second detector material.

18 Claims, 10 Drawing Sheets

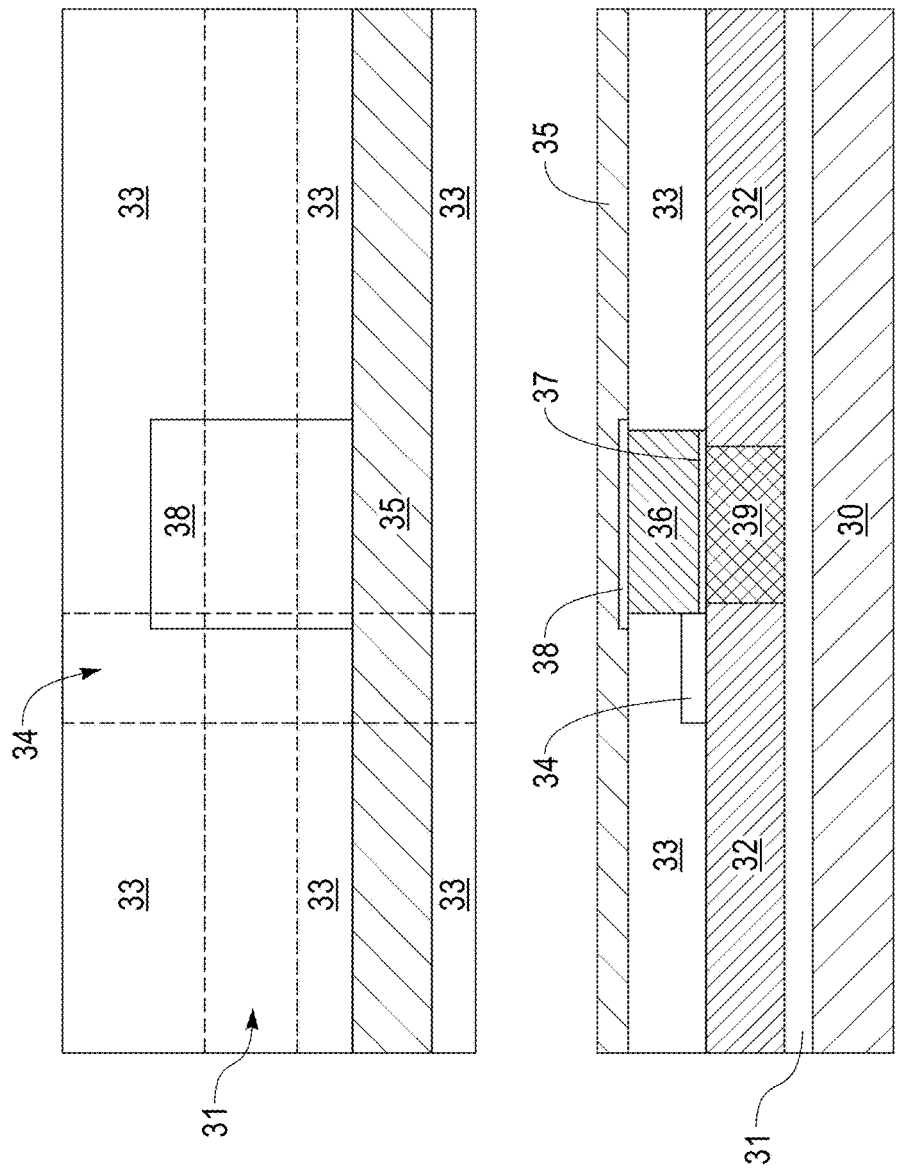

VERTICALLY INTEGRATED MULTISPECTRAL IMAGING SENSOR WITH GRAPHENE AS ELECTRODE AND DIFFUSION BARRIER

TECHNICAL FIELD

Embodiments of the present disclosure are directed to multispectral imaging sensors.

DISCUSSION OF THE RELATED ART

Multispectral imaging is critical for many applications, such as medical imaging and geological surveys. A multispectral image is one that captures image data within a plurality of specific wavelength ranges across the electromagnetic spectrum. FIG. 1 illustrates typical equipment used to acquire a multispectral image. Referring now to the figure, a conventional multispectral detector 10 includes a visual spectrum detector 11, an infrared (IR) detector 12 with an IR aperture 13, and an ultra-violet (UV) detector 14. The multispectral detector 10 also includes a visual and UV aperture 15, a first, adjustable UV mirror 16, a second, fixed UV mirror 18, and a UV channel 19. As can be seen from the figure, separate lenses and filters are required for each detector. There are several challenges associated with a conventional multispectral detector. These include high costs and manufacturing challenges, maintaining optical alignment for multiple channels, and a limited field-of-view.

SUMMARY

Exemplary embodiments of the present disclosure are directed to a vertically integrated multispectral imaging sensor in which graphene is used as an electrode and a diffusion barrier.

According to an embodiment of the disclosure, there is provided a vertically integrated multispectral imaging sensor that includes a first metal contact layer disposed on a substrate, an $SiO_2$ layer on the first metal contact layer with a first detector element embedded in a hole therein, a first graphene layer that covers the first detector element, a second metal contact layer disposed on the $SiO_2$ layer on one side of the first graphene layer where an edge of the second metal contact layer contacts a side of the first graphene layer, an $AlO_3$ layer is disposed on the $SiO_2$ layer, in which a second detector element is embedded in a hole over the first graphene layer, a second graphene layer disposed on the second detector element, and a third metal contact layer disposed on the $AlO_3$ layer adjacent to the second graphene layer, where an edge of the third metal contact layer contacts a side of the second graphene layer. The first detector material is sensitive to a different wavelength band of the electromagnetic spectrum than the second detector material.

According to a further embodiment of the disclosure, the substrate is formed from glass, a silicon wafer, or a flexible material.

According to a further embodiment of the disclosure, the first graphene layer extends past the edge of the first detector element to partially overlap the $SiO_2$ layer.

According to a further embodiment of the disclosure, the first metal contact layer forms a stripe that extends lengthwise on the substrate.

According to a further embodiment of the disclosure, sides of the embedded second detector element are coextensive with sides of the first graphene layer.

According to a further embodiment of the disclosure, the second graphene layer extends past the edge of the second detector element to partially overlap the $AlO_3$ layer.

According to a further embodiment of the disclosure, the second metal contact layer forms a stripe on the $SiO_2$ layer that extends in a widthwise direction perpendicular to the first metal contact layer.

According to a further embodiment of the disclosure, the third metal contact layer forms a stripe on the AlO3 layer that extends in a lengthwise direction perpendicular to the second metal contact layer.

According to a further embodiment of the disclosure, the first detector element and the second detector element are each selected from a group that includes PbSe, PbS, or CdS, where the first detector element differs from the second detector element.

According to a further embodiment of the disclosure, the first metal contact layer, the second metal contact layer, and the third metal contact layer are each formed from a conductive metal.

According to another embodiment of the disclosure, there is provided a method of fabricating a vertically integrated multispectral imaging sensor, including depositing a first metal contact layer on a substrate and patterning the first metal contact layer, depositing an $SiO_2$ layer over the substrate and first metal contact layer, and patterning the $SiO_2$ layer to form a hole that exposes the first metal contact layer in approximately the center of the substrate, depositing a first detector material in the hole, transferring a graphene layer onto the $SiO_2$ layer and patterning the graphene layer to form a first graphene layer that covers the first detector material; depositing and patterning a second metal layer on the $SiO_2$ layer, where the second metal layer is adjacent to and makes contact with the first graphene layer, depositing an $AlO_3$ layer over the $SiO_2$ layer, where no $AlO_3$ accumulates on the first graphene layer to form a hole that surrounds the first graphene layer, depositing a second detector material in the hole on the first graphene layer, transferring another graphene layer onto the $AlO_3$ layer and the second detector material and patterning the graphene layer to form a second graphene layer that covers the second detector material, and depositing and patterning a third metal layer on the $AlO_3$ layer where the third metal layer is adjacent to and makes contact with the second graphene layer. The first detector material is sensitive to a different wavelength band of the electromagnetic spectrum than the second detector material.

According to a further embodiment of the disclosure, the first metal contact layer is patterned to form a stripe that extends lengthwise on the substrate.

According to a further embodiment of the disclosure, upper surfaces of the first detector material and the SiO2 layer are smoothed by a chemical mechanical polishing (CMP) process.

According to a further embodiment of the disclosure, the second metal layer is patterned to form a stripe that extends in a width-wise direction on the $SiO_2$ layer perpendicular to the first metal contact layer.

According to a further embodiment of the disclosure, the third metal contact layer is patterned to form a stripe that extends in a length-wise direction on the $AlO_3$ layer and perpendicular to the second metal contact layer.

According to a further embodiment of the disclosure, the $AlO_3$ layer is deposited by atomic layer deposition (ALD).

According to a further embodiment of the disclosure, the first detector element and the second detector element are each selected from a group that includes PbSe, PbS, or CdS, where the first detector element differs from the second detector element.

According to a further embodiment of the disclosure, the first metal contact layer, the second metal contact layer, and the third metal contact layer are each formed from a conductive metal.

BRIEF DESCRIPTION OF THE DRAWINGS

FIGS. 4-10 illustrate a method of fabricating a vertically integrated multispectral imaging sensor that uses graphene as an electrode and a diffusion barrier, according to an embodiment of the disclosure.

DETAILED DESCRIPTION OF EXEMPLARY EMBODIMENTS

Figure 1:
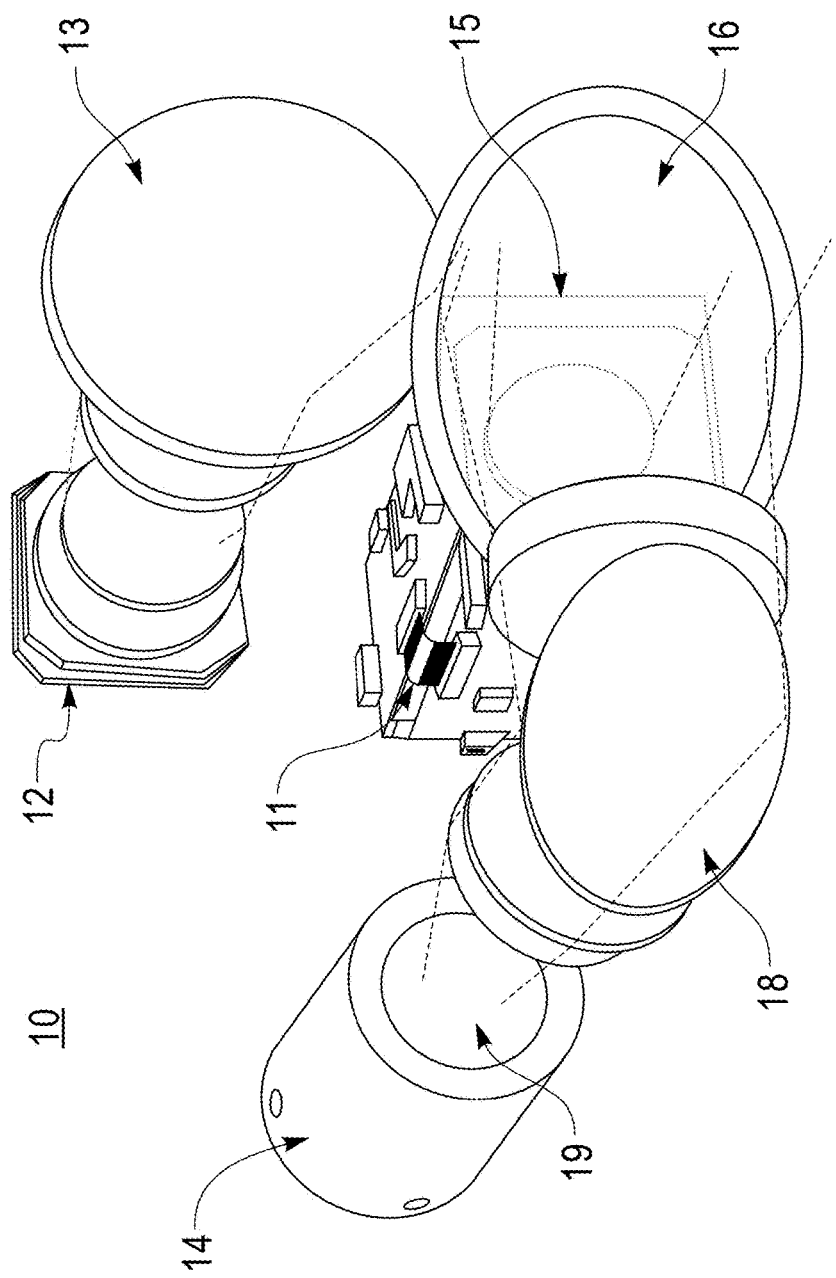
FIG. 1 illustrates a conventional multispectral detector

Exemplary embodiments of the disclosure as described herein generally provide a vertically integrated multispectral imaging sensor. While embodiments are susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

Graphene has been used as a diffusion barrier with selective atomic layer deposition (ALD). Graphene is transparent and highly conductive, as electron and holes move freely within its conduction bands, but the carbon atoms that make up a graphene layer are sufficiently densely packed to prevent atoms and molecules from passing through, thus graphene can act as a diffusion shield. Thus, graphene can be combined with detector materials sensitive to light of different wavelength bands to form a stacked multispectral imaging sensor. Because graphene is transparent, it can be placed between detectors sensitive to different wavelength bands; its conductivity allows a current to flow out to a metal contact, and it acts as a diffusive barrier between the different detectors. Exemplary, non-limiting detectors include PbSe, which has a band gap of ~0.27 eV and is sensitive to near and medium IR in a wavelength band of 3 to about 5 μm, PbS, which has a band gap of ~0.37 eV and is sensitive to near IR in a wavelength band of 1 to about 2.5 μm, and CdS, which has a band gap of ~2.45 eV and is sensitive to visible light, UVA, UVB, and longer wavelength UVC radiation in a wavelength band of 200 to about 600 nm.

Figure 2:
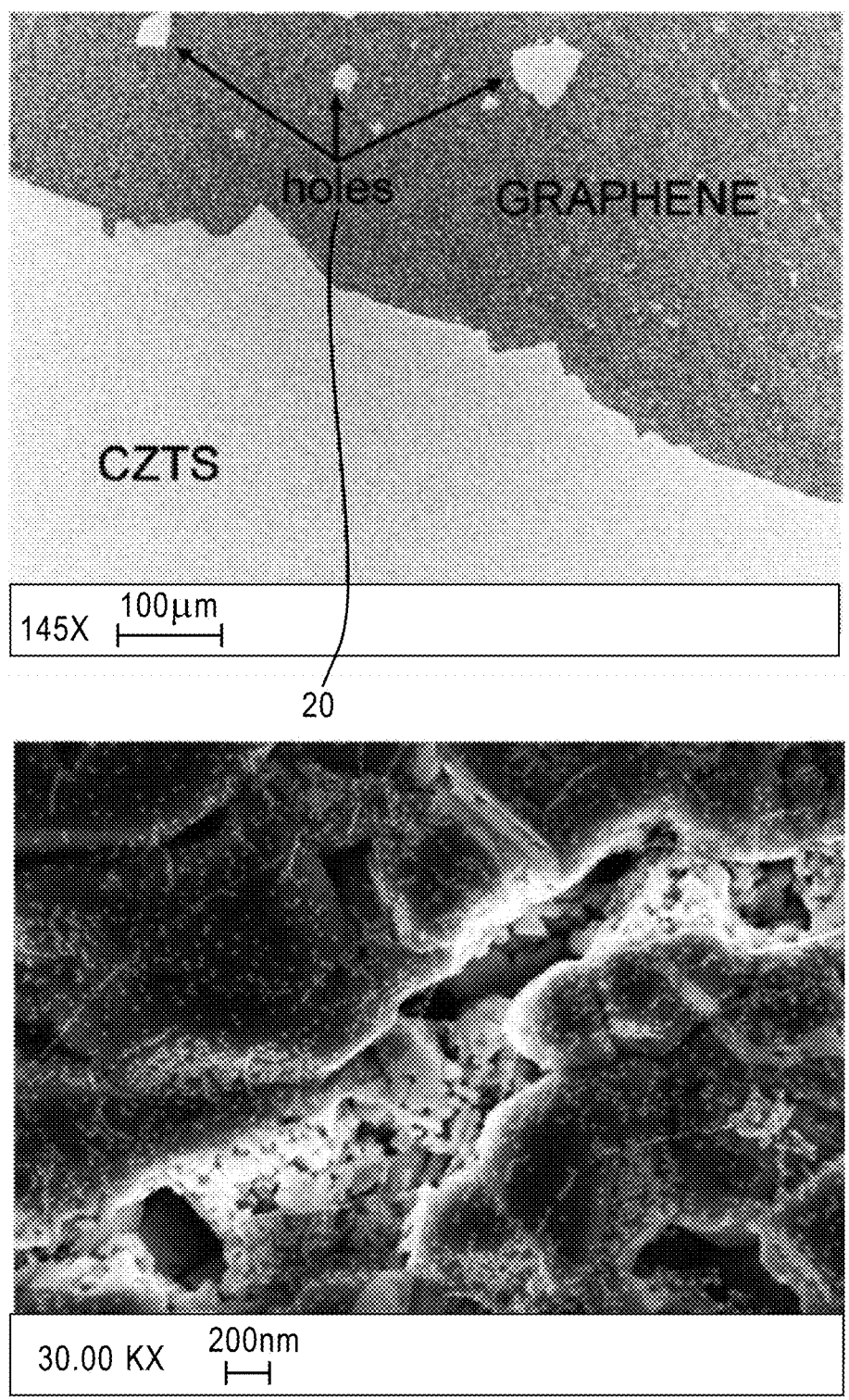
FIG. 2 illustrates the use of graphene as a diffusion barrier with selective ALD, according to an embodiment of the disclosure.

However, it is challenging to form a complete graphene monolayer, as voids form easily. Referring to FIG. 2, the upper image is a scanning electron microscope (SEM) image that shows grapheme on a copper zinc tin sulfide (CZTS) surface after 10 nm of $Al_2O_3$ ALD. The $Al_2O_3$ uniformly coats the CZTS, including exposed CZTS inside holes 20 in the graphene. The graphene surface is not uniformly coated, hence the dark contrast of the image. The lower image is a magnified image of the graphene/CZTS surface, in which exposed CZTS inside cracks, where there is no graphene, is uniformly coated. In contrast, $Al_2O_3$ nucleation on areas covered by graphene are much more sparsely coated.

However, by performing ALD using $AlO_3$, the $AlO_3$ will nucleate in the holes to cover the graphene voids, but will not adhere to the graphene itself, as the graphene, being chemically inert, will not bond with the $AlO_3$. The combination of $AlO_3$ and graphene forms a continuous diffusion barrier. Note that the voids in the graphene do not substantially affect its conductivity, as electron and holes can easily go around the voids.

Figure 3:
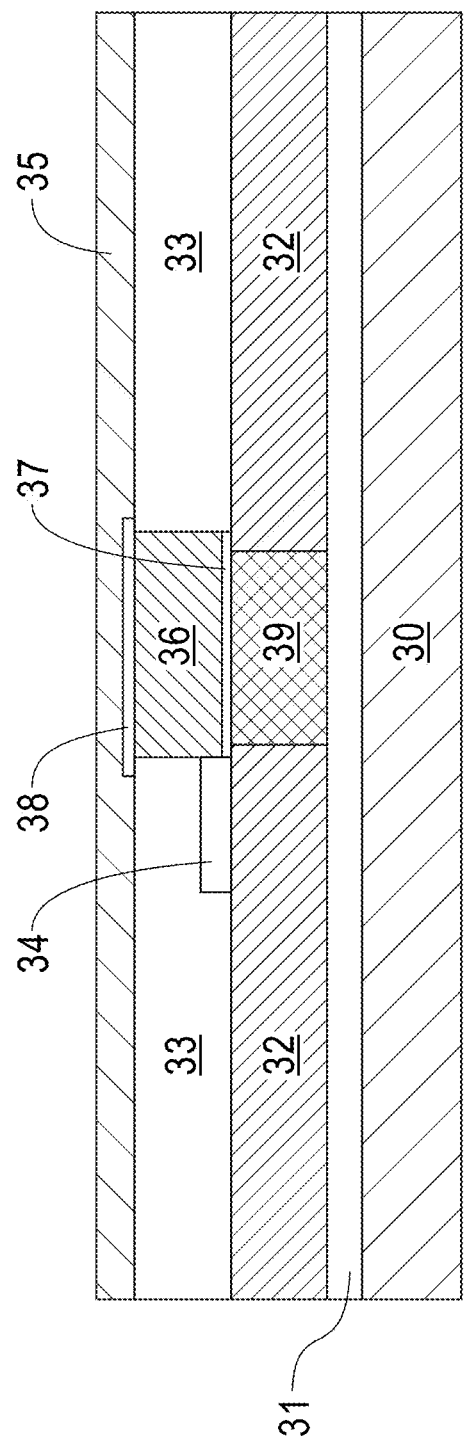
FIG. 3 illustrates a vertically integrated multispectral imaging sensor with graphene as an electrode and diffusion barrier, according to an embodiment of the disclosure.

According to embodiments of the disclosure, a vertically integrated multispectral imaging sensor uses graphene as an electrode and a diffusion barrier. FIG. 3 depicts an exemplary vertically integrated multispectral imaging sensor that uses graphene as an electrode and a diffusion barrier, with two embedded detectors sensitive to different wavelength bands. FIG. 3 depicts two embedded detectors for clarity of exposition and to simplify the drawing, and the concepts involved in a multispectral imaging sensor with two detectors can be extended by those of ordinary skill in the art to a multispectral imaging sensor with three or more detectors. The depiction of a PbSe detector and a PbS detector is exemplary and non-limiting, and either of the two detectors can be replaced with another detector, such as a CdS detector.

Referring now to the figure, a vertically integrated multispectral imaging sensor according to embodiments of the disclosure includes a first metal contact layer 31 on a substrate 30, and a $SiO_2$ layer 32 on the first metal contact layer 31 with an embedded PbSe detector element 39 in a hole in the $SiO_2$ layer 32. The substrate can be glass or a silicon wafer, or a flexible material if required, as long as the material can withstand the temperatures associated with ALD. The metal contact layers serve to interconnect the graphene layers with an external contact to conduct the current generated in the graphene, and can be any suitable conducting metal, such as Cu, Al, or Ag. The first metal contact layer 31 forms a stripe that extends lengthwise on the substrate. The PbSe detector element 39 is covered by a first graphene layer 37 that, in some embodiments, extends past the edge of the PbSe detector element 39 to partially overlap the $SiO_2$ layer 32. The $SiO_2$ layer 32 is covered by an $AlO_3$ layer 33, which has hole over the first graphene layer 37 in which a PbS detector element 36 is embedded on the first graphene layer 37 over the PbSe detector element 39. In some embodiments, the embedded PbS detector element 36 extends so that its sides are coextensive with sides of the first graphene layer 37. A second metal contact layer 34 is disposed between the $SiO_2$ layer 32 and the $AlO_3$ layer 33 on one side of the first graphene layer 37. An edge of the second metal contact layer 34 contacts a side of the first graphene layer 37. The second metal contact layer 34 forms a stripe that extends in a widthwise direction perpendicular to the first metal contact layer 31. A second graphene layer 38 covers the PbS detector element 36, and in some embodiments, the second graphene layer 38 extends past the edge of the PbS detector element 36 to partially overlap the $AlO_3$ layer 33. A third metal contact layer 35 is formed on the $AlO_3$ layer 33 adjacent to the second graphene layer 38. An edge of the third metal contact layer 35 contacts a side of the second graphene layer 38. The third metal contact layer 35 forms a stripe that extends in a lengthwise direction perpendicular to the second metal contact layer 34.

Graphene is used on top of the PbS detector element 36 and between the PbS detector element 36 and the PbSe detector element 39 because the graphene is transparent and can transmit light to lower layers. Since light is not transmitted below the PbSe detector element 39, there is no graphene layer below the PbSe detector element 39.

According to embodiments of the disclosure, in a multispectral imaging sensor of FIG. 3, the graphene layers function as both transparent electrical contacts and as diffusion barriers. A multispectral imaging sensor such as that shown in FIG. 3 has a single optical system with no alignment requirements, and a wide field of view.

Figure 4:
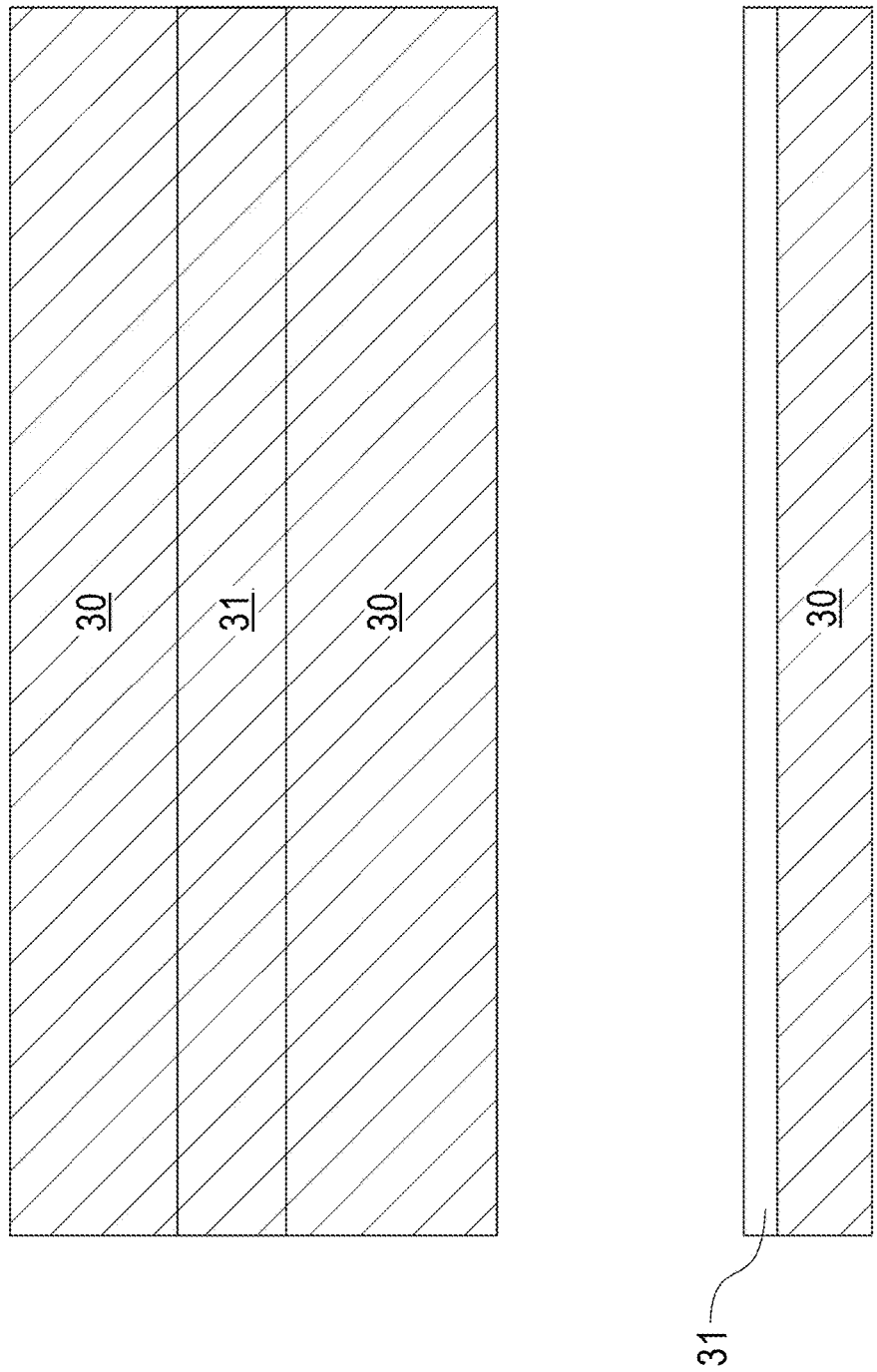
Figure 5:
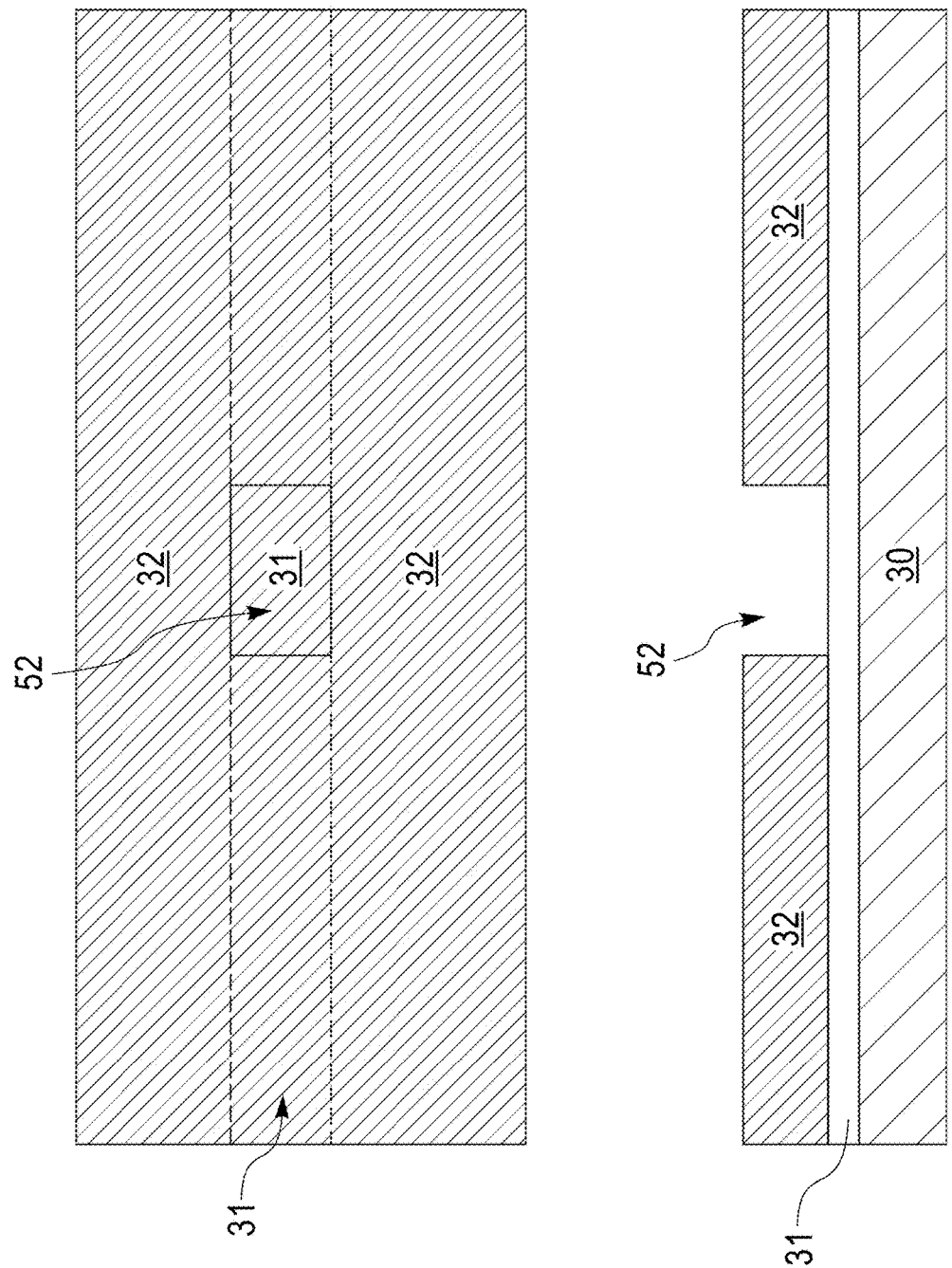
Figure 6:
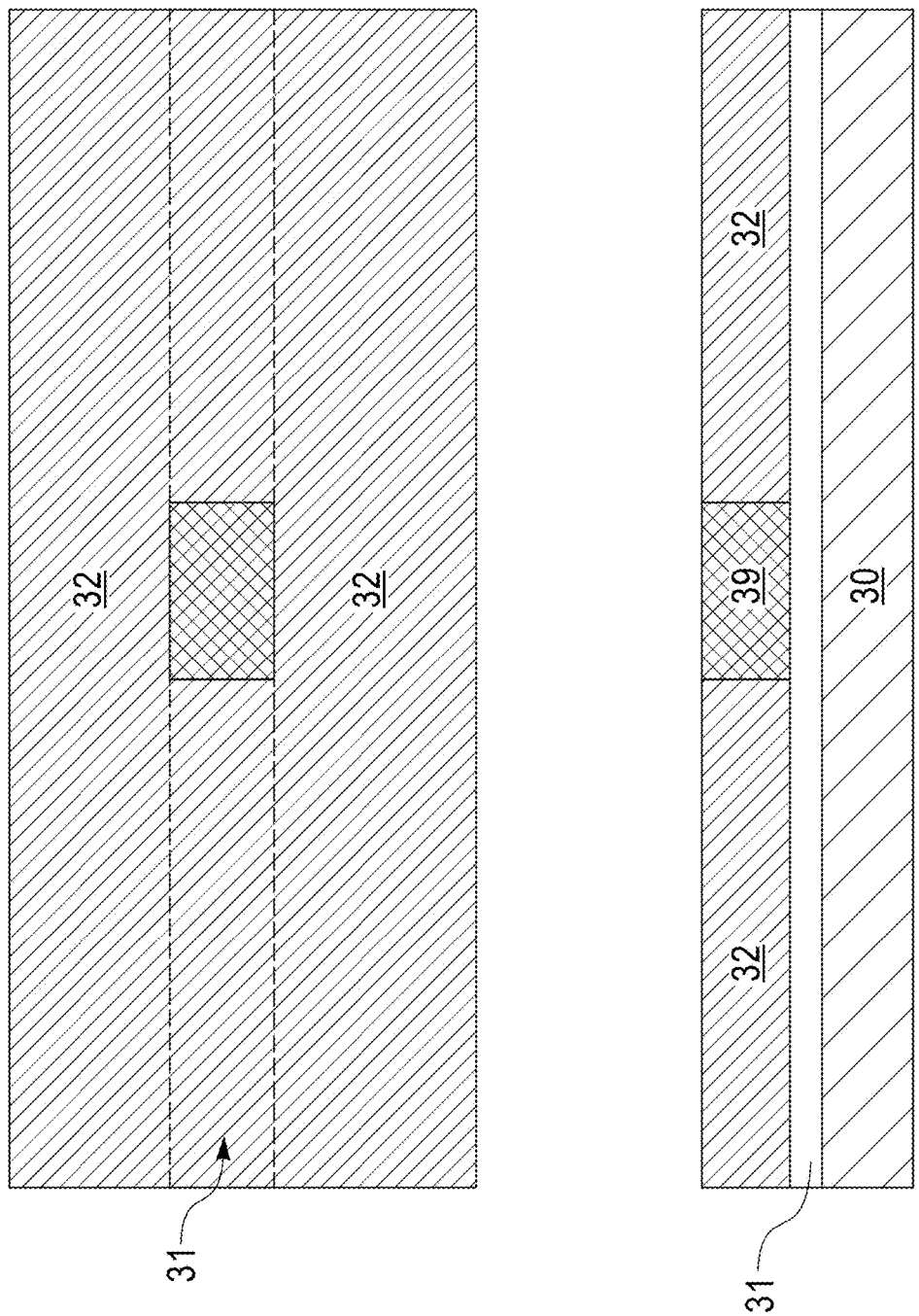

FIGS. 4-10 illustrate a method of fabricating a vertically integrated multispectral imaging sensor with graphene as an electrode and diffusion barrier, according to an embodiment of the disclosure. In each of FIGS. 4-10, the upper image is a plan or top view of the substrate, and the lower image is a cross-sectional view of the substrate in a lengthwise direction along the middle of the substrate. Referring to FIG. 4, a process begins by depositing the first metal contact layer 31 on the substrate 20 and patterning the contact layer 31. The first metal contact layer 31 can be deposited by any suitable process, and is patterned to form a stripe on the substrate. Referring to FIG. 5, the $SiO_2$ layer 32 is deposited and patterned to form a hole 52 that exposes the first metal contact layer 31 in approximately the center of the substrate. Referring to FIG. 6, PbSe material, which has a narrow bandgap, in deposited in the hole 52, and the upper surfaces of the deposited PbSe material and the $SiO_2$ layer 32 are smoothed by a chemical mechanical polishing (CMP) process to form the PbSe detector element 39.

Figure 7:
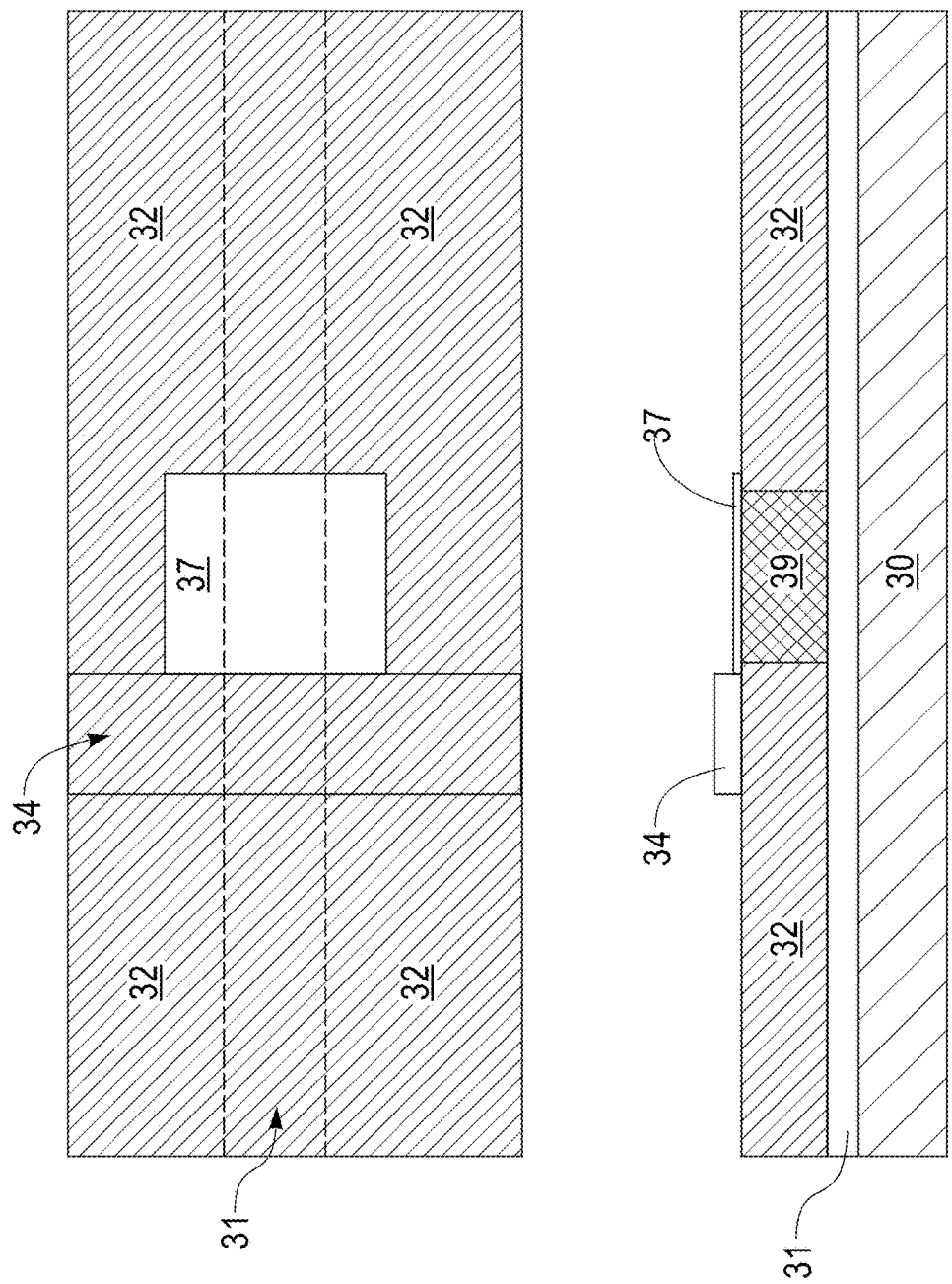

Referring to FIG. 7, a graphene layer is transferred onto the $SiO_2$ layer 32 and patterned to form the first graphene layer 37 that primarily covers the PbSe detector element 39, after which the second metal layer 34 is deposited and patterned. According to embodiments, the graphene is separately grown on a copper film, and is removed from the copper film by known methods and transferred onto the $SiO_2$ layer 32. The second metal layer 34 is patterned to form a stripe that extends in a width-wise direction on the $SiO_2$ layer 32 adjacent to one side of the first graphene layer 37, and perpendicular to the first metal contact layer 31.

Figure 8:
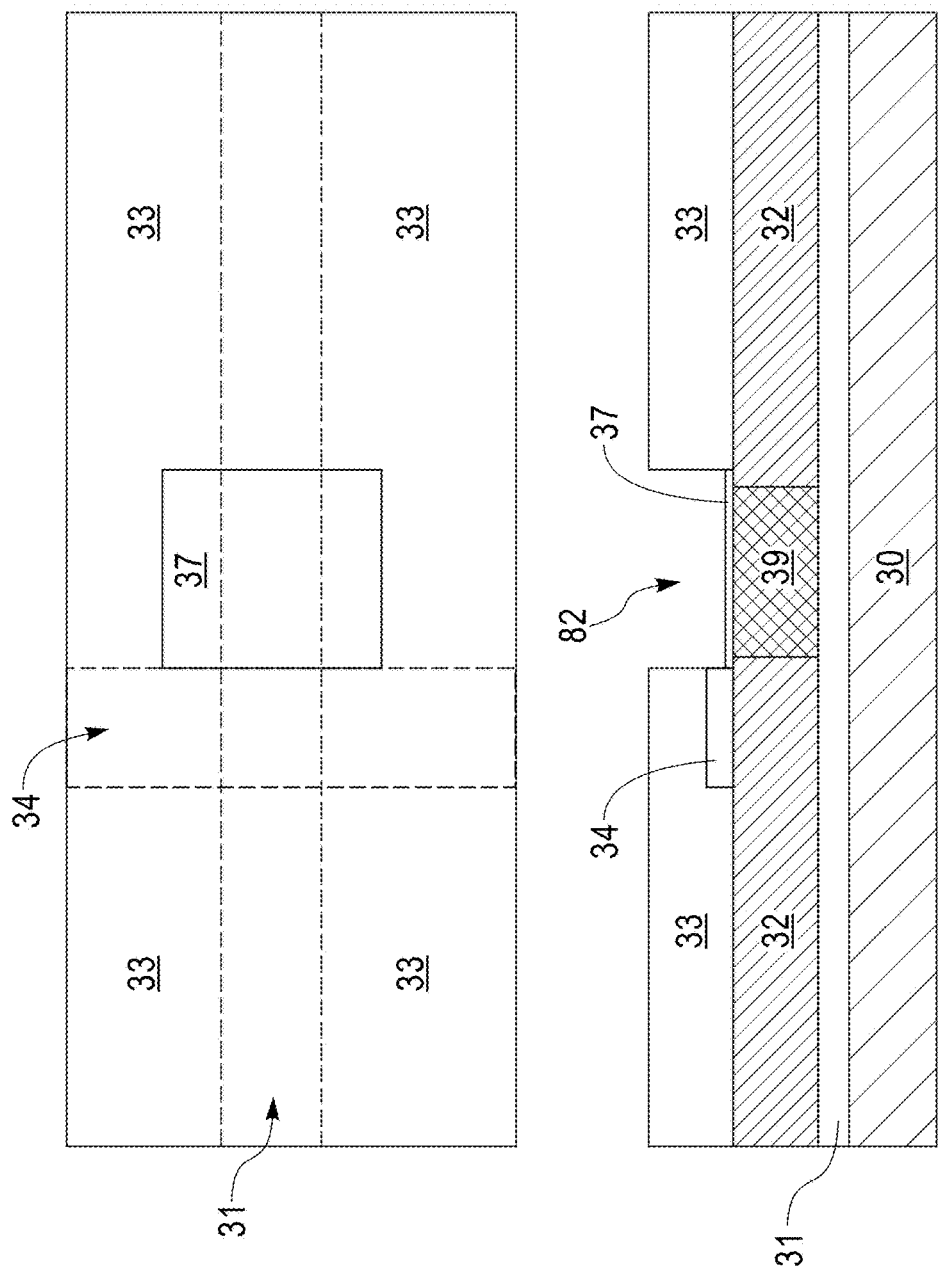
Figure 9:
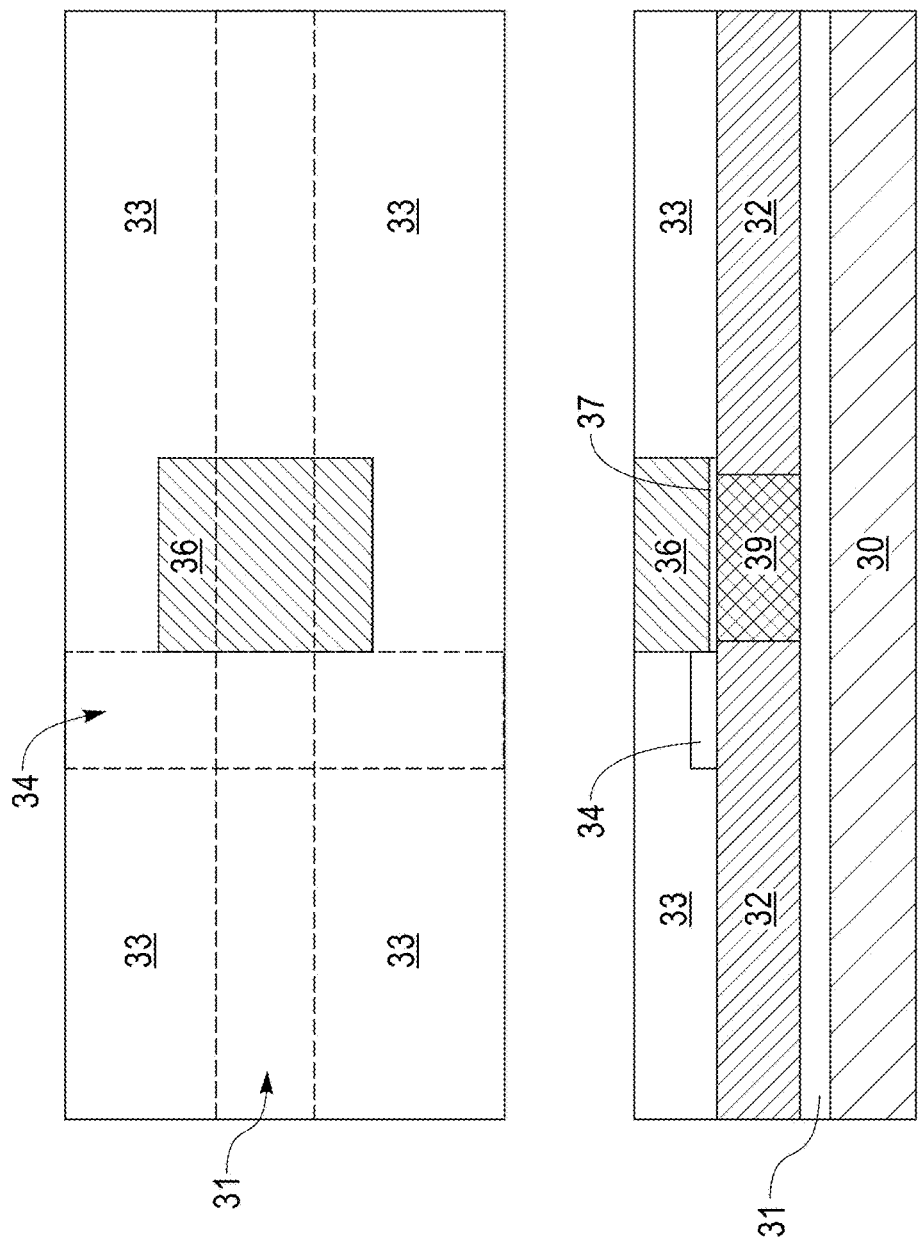

Referring to FIG. 8, the $AlO_3$ layer 33 is deposited by ALD over the $SiO_2$ layer 32. Since the graphene is chemically inert, the $AlO_3$ will not bond to the graphene, and no $AlO_3$ will accumulate on the graphene, forming a hole 82 in which recessed graphene is surrounded by the $AlO_3$ layer 33. However, voids in the first graphene layer 37 are filled with the $AlO_3$ to form a continuous layer. Referring to FIG. 9, PbS, a material with a wider bandgap light sensor than PbSe, is deposited in the hole 82 to form the PbS detector element 36.

Referring to FIG. 10, another graphene layer is transferred onto the $AlO_3$ layer 33 and the PbS detector element 36 and patterned to form the second graphene layer 38 that covers the PbS detector element 3, in a process substantially similar to that used to form the first graphene layer 37. Another metal layer is deposited and patterned to form the third metal contact layer 35 as a stripe that extends in a length-wise direction on the $AlO_3$ layer 33 adjacent to one side of the second graphene layer 38, and perpendicular to the second metal contact layer 34. Since the second graphene layer 38 is a top contact, there is no need to fill in the voids therein.

While embodiments of the present disclosure has been described in detail with reference to exemplary embodiments, those skilled in the art will appreciate that various modifications and substitutions can be made thereto without departing from the spirit and scope of the disclosure as set forth in the appended claims.

What is claimed is:

1. A vertically integrated multispectral imaging sensor, comprising:
 a first metal contact layer disposed on a substrate;
 an $SiO_2$ layer disposed on the first metal contact layer with a first detector element embedded in a hole therein;
 a first graphene layer that covers the first detector element;
 a second metal contact layer disposed on the $SiO_2$ layer on one side of the first graphene layer wherein an edge of the second metal contact layer contacts a side of the first graphene layer;
 an $AlO_3$ layer disposed on the $SiO_2$ layer, in which a second detector element is embedded in a hole over the first graphene layer;
 a second graphene layer disposed on the second detector element; and
 a third metal contact layer disposed on the $AlO_3$ layer adjacent to the second graphene layer, wherein an edge of the third metal contact layer contacts a side of the second graphene layer,
 wherein a material of the first detector element is sensitive to a different wavelength band of the electromagnetic spectrum than a material of the second detector element.

2. The vertically integrated multispectral imaging sensor of claim 1, wherein the substrate is formed from glass, a silicon wafer, or a flexible material.

3. The vertically integrated multispectral imaging sensor of claim 1, wherein the first graphene layer extends past the edge of the first detector element to partially overlap the $SiO_2$ layer.

4. The vertically integrated multispectral imaging sensor of claim 1, wherein the first metal contact layer forms a stripe that extends lengthwise on the substrate.

5. The vertically integrated multispectral imaging sensor of claim 1, wherein sides of the embedded second detector element are coextensive with sides of the first graphene layer.

6. The vertically integrated multispectral imaging sensor of claim 1, wherein the second graphene layer extends past the edge of the second detector element to partially overlap the $AlO_3$ layer.

7. The vertically integrated multispectral imaging sensor of claim 4, wherein the second metal contact layer forms a stripe on the $SiO_2$ layer that extends in a widthwise direction perpendicular to the first metal contact layer.

8. The vertically integrated multispectral imaging sensor of claim 7, wherein the third metal contact layer forms a stripe on the AlO3 layer that extends in a lengthwise direction perpendicular to the second metal contact layer.

9. The vertically integrated multispectral imaging sensor of claim 1, wherein the first detector element and the second detector element are each selected from a group that includes PbSe, PbS, or CdS, wherein the first detector element differs from the second detector element.

10. The vertically integrated multispectral imaging sensor of claim 1, wherein the first metal contact layer, the second metal contact layer, and the third metal contact layer are each formed from a conductive metal.

11. A method of fabricating a vertically integrated multispectral imaging sensor, comprising the steps of:
 depositing a first metal contact layer on a substrate and patterning the first metal contact layer;
 depositing an $SiO_2$ layer over the substrate and first metal contact layer, and patterning the $SiO_2$ layer to form a hole that exposes the first metal contact layer in approximately the center of the substrate;

depositing a first detector material in the hole;

transferring a graphene layer onto the $SiO_2$ layer and patterning the graphene layer to form a first graphene layer that covers the first detector material;

depositing and patterning a second metal layer on the $SiO_2$ layer, wherein the second metal layer is adjacent to and makes contact with the first graphene layer;

depositing an $AlO_3$ layer over the $SiO_2$ layer, wherein no $AlO_3$ accumulates on the first graphene layer to form a hole that surrounds the first graphene layer;

depositing a second detector material in the hole on the first graphene layer;

transferring another graphene layer onto the $AlO_3$ layer and the second detector material and patterning the graphene layer to form a second graphene layer that covers the second detector material; and depositing and patterning a third metal layer on the $AlO_3$ layer wherein the third metal layer is adjacent to and makes contact with the second graphene layer, wherein the first detector material is sensitive to a different wavelength band of the electromagnetic spectrum than the second detector material.

12. The method of claim 11, wherein the first metal contact layer is patterned to form a stripe that extends lengthwise on the substrate.

13. The method of claim 11, wherein upper surfaces of the first detector material and the SiO2 layer are smoothed by a chemical mechanical polishing (CMP) process.

14. The method of claim 12, wherein the second metal layer is patterned to form a stripe that extends in a width-wise direction on the $SiO_2$ layer perpendicular to the first metal contact layer.

15. The method of claim 14, wherein the third metal contact layer is patterned to form a stripe that extends in a length-wise direction on the $AlO_3$ layer and perpendicular to the second metal contact layer.

16. The method of claim 11, wherein the $AlO_3$ layer is deposited by atomic layer deposition (ALD).

17. The method of claim 11, wherein the first detector material and the second detector material are each selected from a group that includes PbSe, PbS, or CdS, wherein the first detector element differs from the second detector element.

18. The method of claim 11, wherein the first metal contact layer, the second metal contact layer, and the third metal contact layer are each formed from a conductive metal.

* * * * *